US00PP20347P2

(12) United States Plant Patent
Skelton

(10) Patent No.: US PP20,347 P2
(45) Date of Patent: Sep. 22, 2009

(54) ***ACTINIDIA CHINENSIS* PLANT NAMED 'Z487'**

(50) Latin Name: *Actinidia chinensis*
Varietal Denomination: Z487

(76) Inventor: Donald Skelton, RD 1 Huntly N.Z., Huntly 3771 (NZ)

( * ) Notice: Subject to any disclaimer, the term of this patent is extended or adjusted under 35 U.S.C. 154(b) by 0 days.

(21) Appl. No.: 12/157,172

(22) Filed: Jun. 6, 2008

(51) Int. Cl.
*A01H 5/00* (2006.01)

(52) U.S. Cl. ..... Plt./226
(58) Field of Classification Search ..... Plt./226
See application file for complete search history.

*Primary Examiner*—Annette H Para

(57) ABSTRACT

A new and distinct *Actinidia chinensis* cultivar named 'Z487' is disclosed, characterized by having distinctive yellow/green flesh fruit, heavy cropping and a seasonal harvest time of late February.

Additionally, the new variety produces fruit with very soft, slight pubescence and with a distinctive blunt stylar end shape and square shoulders. The new variety is suitable for commercial production of kiwi fruit.

4 Drawing Sheets

Latin name of the genus and species: *Actinidia chinensis*.
Variety denomination: 'Z487'.

BACKGROUND OF THE INVENTION

The new cultivar is a product of a planned breeding program, begun in 1975 under the direction of the inventor, Donald Alfred Skelton, a citizen of New Zealand. The seed parent is the unpatented, proprietary seedling variety referred to as *Actinidia chinensis* 'A124' The pollen parent is the unpatented, proprietary seedling variety referred to as *Actinidia chinensis* 'RY.'

Fruit of the new variety was first evaluated in 1999 with favorable results. After the first evaluation, the new variety was grafted onto 5 seedling rootstocks; 3 of *A. chinensis* and 2 of *A. deliciosa*. Subsequent evaluations of the variety have shown the characteristics to be true to type.

SUMMARY OF THE INVENTION

The cultivar 'Z487' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Z487.' These characteristics in combination distinguish 'Z487' as a new and distinct *Actinidia chinensis* cultivar:

1. Distinctive yellow/green flesh fruit.
2. Seasonal harvest time of late February.
3. Very soft, downy pubescence on fruit, with weak adherence to the fruit skin.
4. Oblong fruit shape.
5. Fruit with a distinctive blunt stylar end shape and square shoulders.

COMPARISON TO PARENT

Plants of the new cultivar 'Z487' are similar to plants of the seed parent, *Actinidia chinensis* 'A124' in most horticultural characteristics, however, plants of the new cultivar 'Z487' produce fruit that is narrower, more oblong than obloidAdditionally, fruit of the new variety 'Z487' reaches maturity for harvest approximately 8 weeks earlier than 'A124.'

As the new cultivar is a female, comparison to the pollen parent, is not provided.

COMMERCIAL COMPARISON

The new variety is best compared to the commercial variety, 'Hort16A,' U.S. Plant Pat. No. 11,066. 'Z487' is similar to 'Hort16A' in many horticultural characteristics, however, 'Z487' produces mature approximately 10 weeks earlier than 'Hort16A.' Additionally, the new variety produces an a broader fruit shape. Fruit of the new variety'Z487' are distinctively blunt on the stylar end, compared to the strong pointed stylar end shape of 'Hort16.' Fruit shape differences can also be noted in the shoulder shape. Whereas 'Z487' produces fruit with strongly squared shoulder, 'Hort16A' fruit have rounded shoulders.

BRIEF DESCRIPTION OF THE PHOTOGRAPH

The accompanying photograph in FIG. 1 illustrates in full color typical foliage and flowers on plants of 'Z487.'

Figure 1:
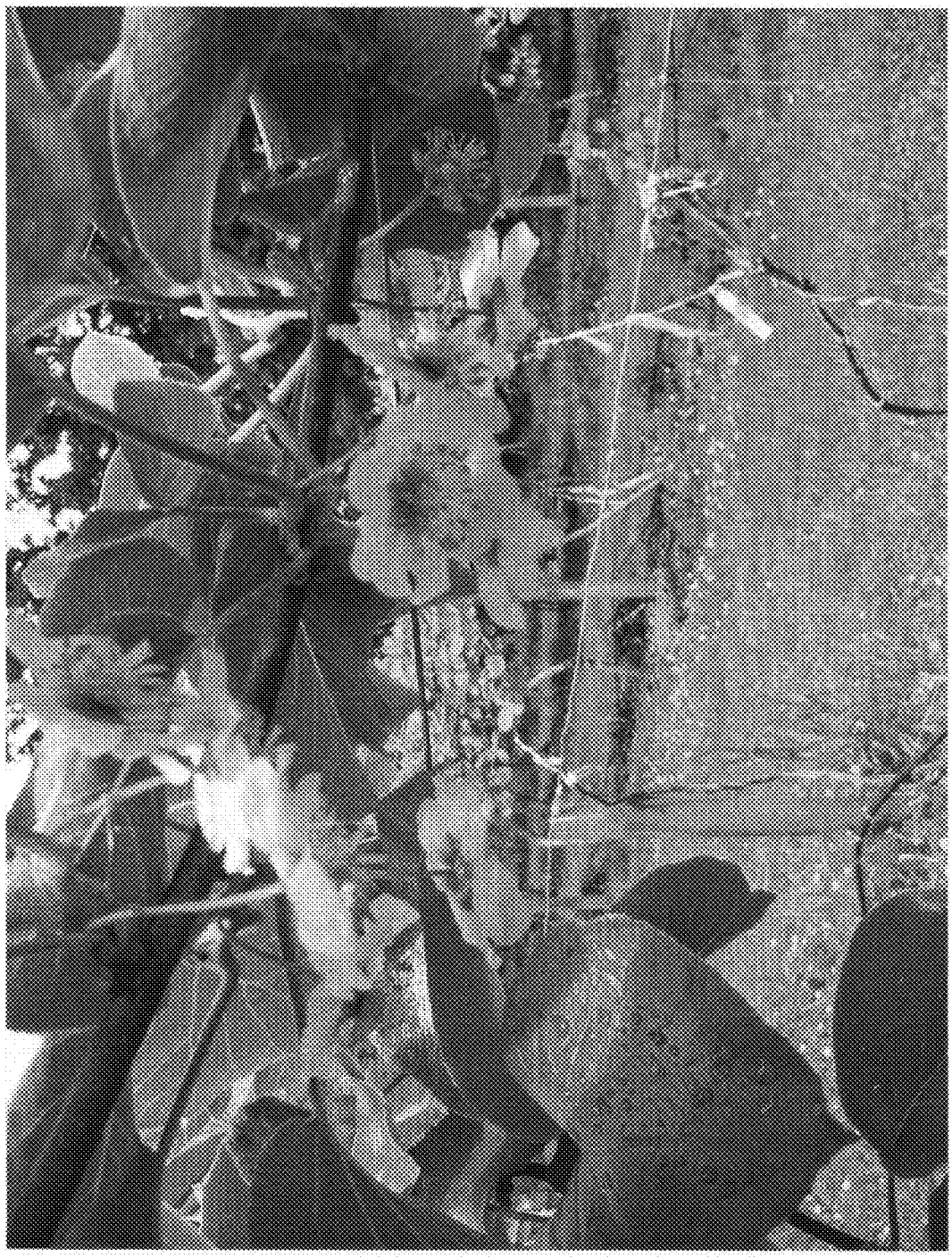
Figure 2:
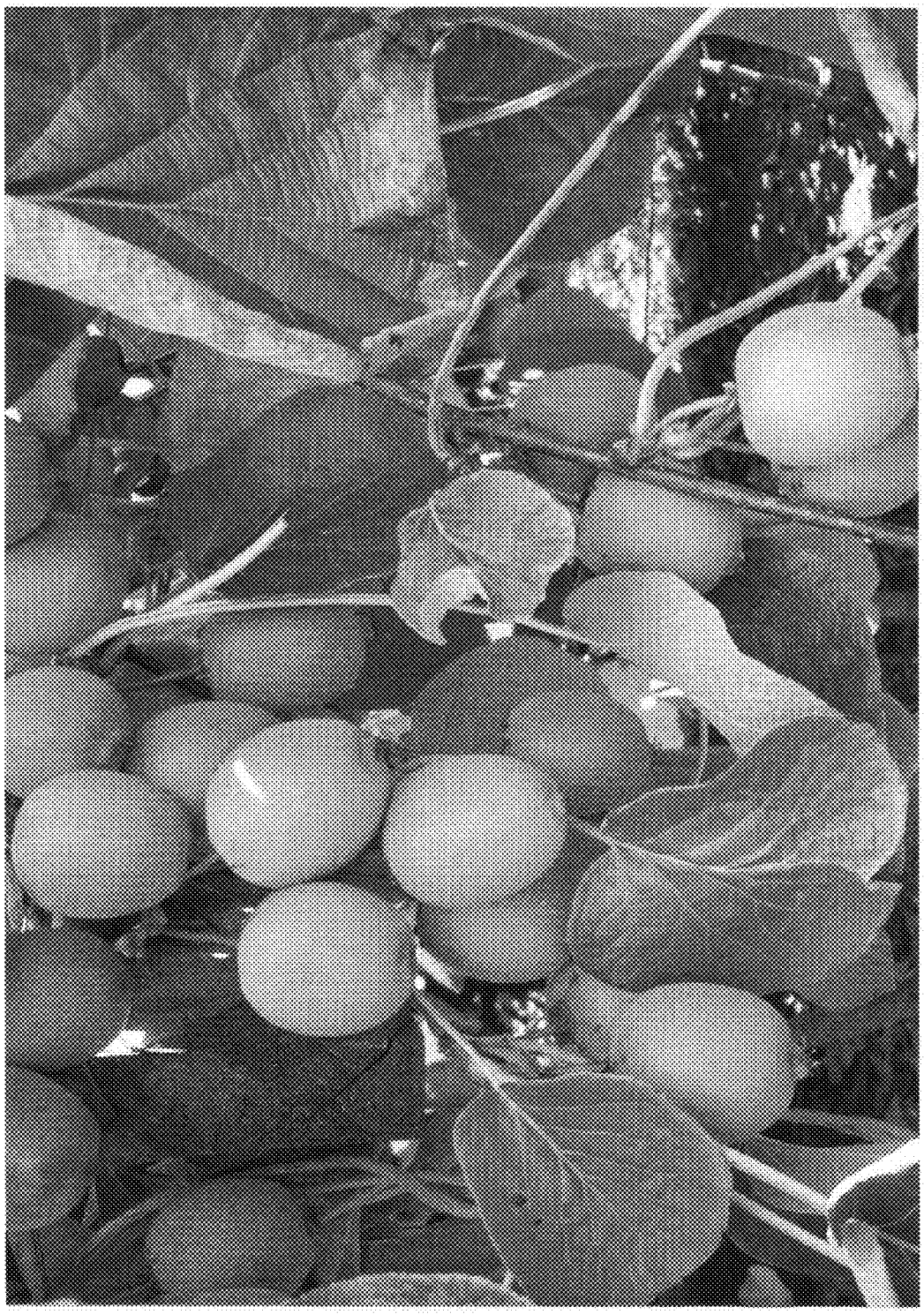
FIG. 2 illustrates in full color typical fruit, on the plant of 'Z487.'
Figure 3:
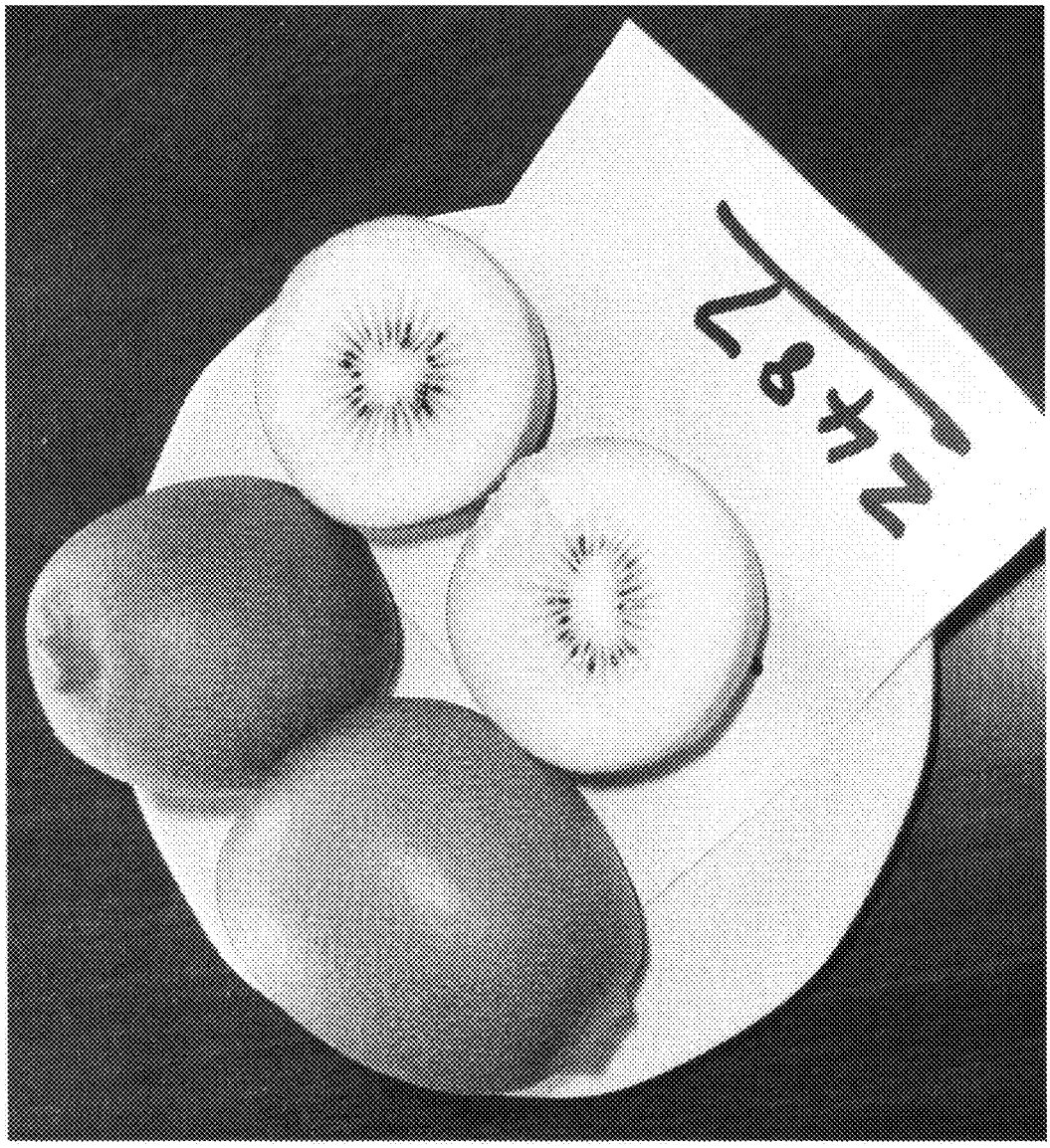
FIG. 3 shows examples of typical fruit harvested from 'Z487.'
Figure 4:
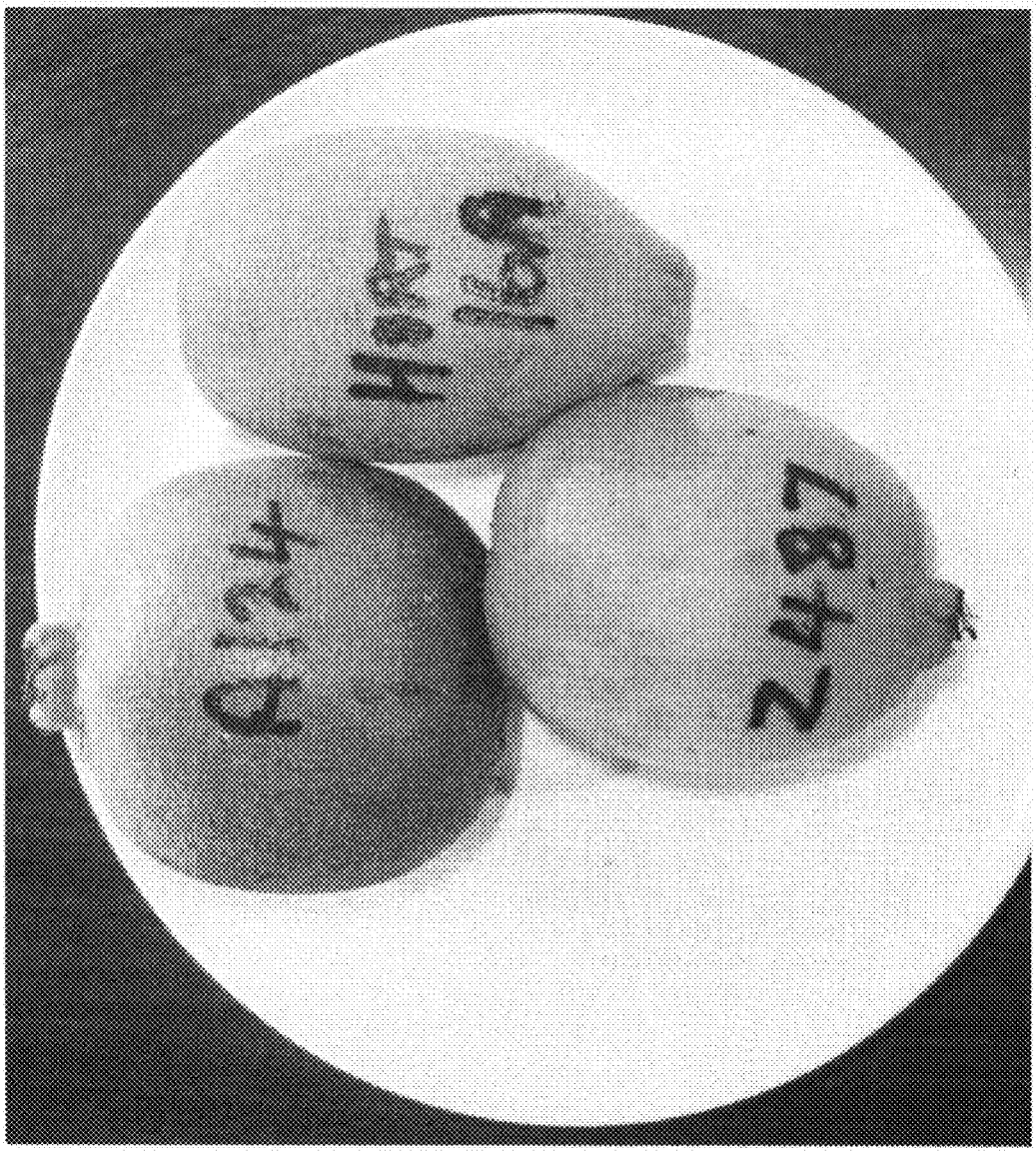
FIG. 4 is a comparison of fruit of similar varieties, including the female parent 'A124' and the commercial comparison, 'Hort16A.'

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Z487' plants grown under outdoor commercial trial conditions in Rangiriri New Zealand. The growing temperature ranged from 10° C. to 25° C. with no precipitation. Measurements and numerical values represent averages of typical plant types.

Botanical classification: *Actinidia chinensis* cultivar 'Z487.'

PROPAGATION:

'Z487' can be successfully grafted onto rootstocks of *Actnidia chinensis* or *Actinidia deliciosa.*

PLANT

*Age of the plant described.*—Approximately 5 years.
*Height of the plant described.*—Approximately 2 years.
*Width of the plant described.*—Approximately 4 meters.
*Rootstock of plant described.*—Actinidia chinensis.
*Sex expression.*—Female.
*Ploidy.*—Diploid.

FOLIAGE

Leaf:

*Average length.*—Approximately 15.5 cm.
*Average width.*—Approximately 16.0 cm.
*Shape of blade.*—Very broadly ovate.
*Apex.*—Rounded.
*Base.*—Cordate, not overlapping.
*Attachment.*—Petioled.
*Margin.*—Ciliate.
*Texture of top surface.*—Very slightly puckered.
*Texture of under side.*—Moderately glossy, non-pubescent.
*Color.*—Mature foliage upper side: Near RHS Green 141A. Mature foliage under side: Near RHS Green 141C.
*Petiole.*—Length: Range between 14.0–15.3 cm. Pubescence: None. Other characteristics: Moderate anthocyanin on upperside of petiole.

FLOWER

*Bud break.*—Late August.
*First flower.*—Mid October.
*Diameter.*—Average 4.5 cm.
*Petal quantity.*—6 to 10 per flower.
*Petals overlapping.*—Yes.
*Primary color.*—White.
*Filament color.*—White.
*Anther color.*—Brown.
*Attitude of styles.*—Semi-erect.
*Hair on ovary.*—Dense.
*Color of ovary.*—White.
*Number of sepals.*—6 to 10.
*Color of sepals.*—Near RHS Green 141C.
*Margin of sepals.*—Entire.
*Apex of sepals.*—Acute.
*Base of sepals.*—Truncate.

FRUIT

*Color outer pericarp.*—Near RHS Yellow-Green 154C.
*Color inner pericarp.*—Near RHS Yellow-Green 1D.
*Core color.*—Near RHS White 158D.
*Brix at consumption.*—Minimum 16.0.
*Brix at harvest.*—Average 7.60%.
*Average weight.*—100.9 grams.
*Minimum weight.*—85 grams.
*Maximum weight.*—115 grams.
*Length.*—Avg. 65 mm.
*Width.*—Avg. 55 mm.
*Core diameter(maximum).*—12.0 mm.
*Core diameter(minimum).*—5.0 mm.
*Locule number.*—32.
*Fruit peduncle length.*—35–45 mm.
*Fruit peduncle width.*—3.0–4.0 mm.
*General shape.*—Oblong.
*Median cross section.*—Circular.
*Stylar end shape.*—Slightly blunt protruding.
*Shoulder shape.*—Squared.
*Calyx ring.*—Present.
*Calyx ring expression.*—Strong, 13–16 mm diameter.
*Skin color at harvest.*—Near RHS Grey-Orange 165D.
*Hair on fruit skin.*—Downy.
*Hair adherence to skin.*—Weak.
*Fruit core shape.*—Elliptic.
*Core-woody spike.*—Small.
*Mature seed color.*—Black.
*Dried seed.*—Brown.
*Harvest time.*—Late February.
*Overall cropping quantity.*—25 to 35 tons per hectare.

OTHER CHARACTERISTICS

Storage life: Storage life is a minimum of 3 months at 2° C.
Disease/pest resistance: Neither resistance nor susceptibility to pathogens and pests common to *Actinidia chinensis* have been observed.

What is claimed is:

1. A new and distinct cultivar of *Actinidia chinensis* plant named 'Z487' as herein illustrated and described.

* * * * *